(12) United States Patent
Esch et al.

(10) Patent No.: US 9,770,297 B2
(45) Date of Patent: Sep. 26, 2017

(54) ENERGY DEVICES AND METHODS FOR TREATING HOLLOW ANATOMICAL STRUCTURES

(75) Inventors: Brady David Esch, San Jose, CA (US); Brian Eugene Farley, Los Altos, CA (US)

(73) Assignee: Covidien LP, Mansfield, MA (US)

( * ) Notice: Subject to any disclaimer, the term of this patent is extended or adjusted under 35 U.S.C. 154(b) by 2611 days.

(21) Appl. No.: 12/478,663

(22) Filed: Jun. 4, 2009

(65) Prior Publication Data

US 2009/0306637 A1 Dec. 10, 2009

Related U.S. Application Data

(60) Provisional application No. 61/058,874, filed on Jun. 4, 2008.

(51) Int. Cl.
| | |
|---|---|
| *A61B 18/24* | (2006.01) |
| *A61B 18/28* | (2006.01) |
| *A61B 17/00* | (2006.01) |
| *A61B 18/22* | (2006.01) |
| *A61B 90/00* | (2016.01) |

(52) U.S. Cl.
CPC ............ *A61B 18/24* (2013.01); *A61B 18/28* (2013.01); *A61B 2017/00084* (2013.01); *A61B 2018/2211* (2013.01); *A61B 2018/2261* (2013.01); *A61B 2018/2272* (2013.01); *A61B 2090/0811* (2016.02)

(58) Field of Classification Search
USPC ................................. 606/2–19; 385/134–140
See application file for complete search history.

(56) References Cited

U.S. PATENT DOCUMENTS

| | | |
|---|---|---|
| 373,399 A | 11/1887 | Hamilton |
| 659,409 A | 10/1900 | Mosher |
| 833,759 A | 10/1906 | Sourwine |
| 985,865 A | 3/1911 | Turner, Jr. |
| 2,671,444 A | 3/1954 | Pease, Jr. |
| 3,230,957 A | 1/1966 | Seifert |
| 3,301,258 A | 1/1967 | Werner et al. |
| 3,557,794 A | 1/1971 | Van Patten |
| 3,920,021 A | 11/1975 | Hiltebrandt |
| 4,016,886 A | 4/1977 | Doss et al. |

(Continued)

FOREIGN PATENT DOCUMENTS

| | | |
|---|---|---|
| CN | 1050992 | 5/1991 |
| EP | 0189329 | 7/1986 |

(Continued)

OTHER PUBLICATIONS

Biegelesian, K., "Use of the Venoscope for the Treatment of Varicose Veins," Phlebologie 1989, pp. 419-422.

(Continued)

*Primary Examiner* — William Thomson
*Assistant Examiner* — Vynn Huh

(57) ABSTRACT

Apparatus and methods for segmental treatment of hollow anatomical structures using an optical fiber are disclosed. An elongate energy application device can absorb, scatter and/or reflect laser energy over a length of the elongate energy application device to thereby treat the hollow anatomical structure along one or more lengthened treatment segments.

21 Claims, 9 Drawing Sheets

(56) References Cited

U.S. PATENT DOCUMENTS

| | | | |
|---|---|---|---|
| 4,043,338 A | 8/1977 | Homm et al. | |
| 4,119,102 A | 10/1978 | LeVeen | |
| 4,154,246 A | 5/1979 | LeVeen | |
| 4,312,364 A | 1/1982 | Convert et al. | |
| 4,436,715 A | 3/1984 | Schaap et al. | |
| 4,522,205 A | 6/1985 | Taylor et al. | |
| 4,643,186 A | 2/1987 | Rosen et al. | |
| 4,646,737 A * | 3/1987 | Hussein et al. | 606/28 |
| 4,648,865 A | 3/1987 | Aigner | |
| 4,658,836 A | 4/1987 | Turner | |
| 4,660,571 A | 4/1987 | Hess et al. | |
| 4,664,120 A | 5/1987 | Hess | |
| 4,699,147 A | 10/1987 | Chilson et al. | |
| 4,709,698 A | 12/1987 | Johnston et al. | |
| 4,765,331 A | 8/1988 | Petruzzi et al. | |
| 4,773,413 A | 9/1988 | Hussein et al. | |
| 4,776,349 A | 10/1988 | Nashef et al. | |
| 4,802,650 A | 2/1989 | Stricker | |
| 4,807,620 A | 2/1989 | Strul et al. | |
| 4,823,812 A | 4/1989 | Eshel et al. | |
| 4,862,887 A | 9/1989 | Weber et al. | |
| 4,937,711 A | 6/1990 | Shuen | |
| 4,945,912 A | 8/1990 | Langberg | |
| 4,966,597 A | 10/1990 | Cosman | |
| 4,979,948 A | 12/1990 | Geddes et al. | |
| 5,010,894 A | 4/1991 | Edhag | |
| 5,022,399 A | 6/1991 | Biegeleisen | |
| 5,035,694 A | 7/1991 | Kasprzyk et al. | |
| 5,053,033 A | 10/1991 | Clarke | |
| 5,057,106 A | 10/1991 | Kasevich et al. | |
| 5,057,107 A | 10/1991 | Parins et al. | |
| 5,078,717 A | 1/1992 | Parins et al. | |
| 5,098,429 A | 3/1992 | Sterzer | |
| 5,098,431 A | 3/1992 | Rydell | |
| 5,117,828 A | 6/1992 | Metzger et al. | |
| 5,122,137 A | 6/1992 | Lennox | |
| 5,155,602 A | 10/1992 | Terajima | |
| 5,156,151 A | 10/1992 | Imran | |
| 5,158,560 A | 10/1992 | Sogawa et al. | |
| 5,188,602 A | 2/1993 | Nichols | |
| 5,190,517 A | 3/1993 | Zieve et al. | |
| 5,193,549 A | 3/1993 | Bellin et al. | |
| 5,215,103 A | 6/1993 | Desai | |
| 5,255,678 A | 10/1993 | Deslauriers et al. | |
| 5,263,493 A | 11/1993 | Avitall | |
| 5,275,610 A | 1/1994 | Eberbach | |
| 5,281,218 A | 1/1994 | Imran | |
| 5,282,845 A | 2/1994 | Bush et al. | |
| 5,293,869 A | 3/1994 | Edwards et al. | |
| 5,314,466 A | 5/1994 | Stern et al. | |
| 5,318,024 A | 6/1994 | Kittrell et al. | |
| 5,324,285 A | 6/1994 | Cannon | |
| 5,330,465 A * | 7/1994 | Doiron et al. | 606/7 |
| 5,354,324 A | 10/1994 | Gregory | |
| 5,370,677 A | 12/1994 | Rudie et al. | |
| 5,370,678 A | 12/1994 | Edwards et al. | |
| 5,383,917 A | 1/1995 | Desai et al. | |
| 5,397,339 A | 3/1995 | Desai | |
| 5,403,312 A | 4/1995 | Yates et al. | |
| 5,405,322 A | 4/1995 | Lennox et al. | |
| 5,405,346 A | 4/1995 | Grundy et al. | |
| 5,409,000 A | 4/1995 | Imran | |
| 5,411,025 A | 5/1995 | Webster, Jr. | |
| 5,423,815 A | 6/1995 | Fugo | |
| 5,429,130 A | 7/1995 | Goldman | |
| 5,431,649 A | 7/1995 | Mulier et al. | |
| 5,437,660 A | 8/1995 | Johnson et al. | |
| 5,437,664 A | 8/1995 | Cohen et al. | |
| 5,445,608 A | 8/1995 | Chen et al. | |
| 5,445,680 A | 8/1995 | Hamilton | |
| 5,447,529 A | 9/1995 | Marchlinski et al. | |
| 5,449,381 A | 9/1995 | Imran | |
| 5,454,809 A | 10/1995 | Janssen | |
| 5,458,596 A | 10/1995 | Lax et al. | |
| 5,462,545 A | 10/1995 | Wang et al. | |
| 5,465,717 A | 11/1995 | Imran et al. | |
| 5,468,242 A | 11/1995 | Reisberg | |
| 5,472,441 A | 12/1995 | Edwards et al. | |
| 5,505,730 A | 4/1996 | Edwards | |
| 5,514,130 A | 5/1996 | Baker | |
| 5,531,739 A | 7/1996 | Trelles | |
| 5,545,161 A | 8/1996 | Imran | |
| 5,562,657 A | 10/1996 | Griffin | |
| 5,607,422 A | 3/1997 | Smeets et al. | |
| 5,626,578 A | 5/1997 | Tihon | |
| 5,643,251 A | 7/1997 | Hillsman et al. | |
| 5,681,310 A | 10/1997 | Yuan et al. | |
| 5,709,224 A | 1/1998 | Behl et al. | |
| 5,766,176 A | 6/1998 | Duncan | |
| 5,794,628 A | 8/1998 | Dean | |
| 5,810,804 A | 9/1998 | Gough et al. | |
| 5,814,048 A | 9/1998 | Morgan | |
| 5,817,092 A | 10/1998 | Behl | |
| 5,863,290 A | 1/1999 | Gough et al. | |
| 5,868,740 A | 2/1999 | LeVeen et al. | |
| 5,885,278 A | 3/1999 | Fleischman | |
| 5,899,882 A * | 5/1999 | Waksman et al. | 604/103.07 |
| 5,944,713 A * | 8/1999 | Schuman | A61B 18/24 606/10 |
| 5,968,038 A * | 10/1999 | Djeu | A61B 18/28 606/13 |
| 6,004,316 A | 12/1999 | Laufer | |
| 6,033,397 A | 3/2000 | Laufer et al. | |
| 6,033,398 A | 3/2000 | Farley et al. | |
| 6,036,687 A | 3/2000 | Laufer et al. | |
| 6,071,277 A | 6/2000 | Farley et al. | |
| 6,071,291 A | 6/2000 | Forst et al. | |
| 6,129,698 A | 10/2000 | Beck | |
| 6,135,997 A | 10/2000 | Laufer et al. | |
| 6,138,046 A | 10/2000 | Dalton | |
| 6,139,527 A | 10/2000 | Laufer et al. | |
| 6,152,899 A | 11/2000 | Farley et al. | |
| 6,156,032 A | 12/2000 | Lennox | |
| 6,401,719 B1 | 6/2002 | Farley et al. | |
| 6,572,609 B1 | 6/2003 | Farr et al. | |
| 6,611,488 B1 * | 8/2003 | Odajima | B82Y 10/00 369/112.06 |
| 6,613,045 B1 | 9/2003 | Laufer et al. | |
| 6,638,273 B1 | 10/2003 | Farley et al. | |
| 6,652,585 B2 | 11/2003 | Lange | |
| 6,769,433 B2 | 8/2004 | Zikorus et al. | |
| 6,800,092 B1 | 10/2004 | Williams et al. | |
| 6,845,193 B2 | 1/2005 | Loeb et al. | |
| 6,969,388 B2 | 11/2005 | Goldman et al. | |
| 6,981,972 B1 | 1/2006 | Farley et al. | |
| 7,160,289 B2 | 1/2007 | Cohen | |
| 7,163,533 B2 | 1/2007 | Hobbs et al. | |
| 7,201,748 B2 | 4/2007 | Karino et al. | |
| 7,273,478 B2 | 9/2007 | Appling et al. | |
| 7,396,355 B2 | 7/2008 | Goldman et al. | |
| 7,458,967 B2 | 12/2008 | Appling et al. | |
| 7,524,316 B2 | 4/2009 | Hennings et al. | |
| 2001/0037080 A1 | 11/2001 | Mueller et al. | |
| 2002/0123750 A1 | 9/2002 | Eisermann et al. | |
| 2004/0049175 A1 | 3/2004 | Speck et al. | |
| 2004/0092913 A1 | 5/2004 | Hennings et al. | |
| 2005/0054983 A1 | 3/2005 | Mullen | |
| 2005/0119645 A1* | 6/2005 | Shafirstein et al. | 606/28 |
| 2005/0215988 A1 | 9/2005 | Altshuler et al. | |
| 2005/0259933 A1 | 11/2005 | Temelkuran et al. | |
| 2005/0288655 A1 | 12/2005 | Root et al. | |
| 2006/0104593 A1* | 5/2006 | Gowda et al. | 385/140 |
| 2006/0167442 A1 | 7/2006 | Herbert et al. | |
| 2007/0049999 A1 | 3/2007 | Esch et al. | |
| 2007/0100329 A1 | 5/2007 | Maglione et al. | |
| 2007/0179486 A1 | 8/2007 | Welch et al. | |
| 2007/0196414 A1 | 8/2007 | Hammarsten et al. | |
| 2008/0065058 A1 | 3/2008 | Neuberger | |
| 2008/0125705 A1 | 5/2008 | Sato et al. | |
| 2008/0188843 A1 | 8/2008 | Appling et al. | |
| 2008/0208180 A1 | 8/2008 | Cartier et al. | |
| 2008/0287939 A1 | 11/2008 | Appling et al. | |
| 2009/0088695 A1 | 4/2009 | Kapur et al. | |
| 2009/0131924 A1 | 5/2009 | Meyer et al. | |

(56) References Cited

U.S. PATENT DOCUMENTS

FOREIGN PATENT DOCUMENTS

| | | |
|---|---|---|
| EP | 0205851 | 12/1986 |
| EP | 0629382 | 12/1994 |
| EP | 0738501 | 10/1996 |
| WO | WO 90/07303 | 7/1990 |
| WO | WO 92/12681 | 8/1992 |
| WO | WO 93/21846 | 11/1993 |
| WO | WO 94/07446 | 4/1994 |
| WO | WO 94/21170 | 9/1994 |
| WO | WO 95/10322 | 4/1995 |
| WO | WO 95/10978 | 4/1995 |
| WO | WO 95/31142 | 11/1995 |
| WO | WO 96/32885 | 10/1996 |
| WO | WO 97/06739 | 2/1997 |
| WO | WO 97/17892 | 5/1997 |
| WO | WO 98/55072 | 12/1998 |

OTHER PUBLICATIONS

Brunelle et al., "A Bipolar Electrode for Vascular Electrocoagulation with Alternating Current," Radiology, vol. 137, pp. 239-240, Oct. 1980.

Cragg et al., "Endovascular Diathermic Vessel Occlusion," Diagnostic Radiology, vol. 144, pp. 303-308, Jul. 1982.

Crockett et al., "Preliminary Experience with an Endovascular Catheter for Electrocoagulation of Peripheral Veins," The Journal of Vascular Technology, vol. 20, No. 1, pp. 19-22, Winter.

Examination Report from European Patent Office (EPO) dated Dec. 2, 2010 for European Patent Application No. 08 746 951.6, filed Apr. 25, 2008.

Gradman, Venoscopic Obliteration of Variceal Tributaries Using Monopolar Electrocautery, Journal of Dermatology Surgery Oncology, 1994, 20, p. 482-485 (Abstract).

Milostanov, "Endovascular Electrocoagulation: The Operation of Choice in Treating Varicose Veins of the Lower Extremities," All Russia Conference of Surgeons Specializing in Phlebology, Saratov, Sep. 12-15, 1966.

Money, "Endovascular Electroblation of Peripheral Veins," 22nd Annual Symposium on Current Critical Problems, New Horizons and Techniques in Vascular and Endovascular Surgery, Nov. 16-19, 1995.

Office Action from the State Intellectual Property Office of the P.R.C (SIPO) for application No. 200880013423, dated Mar. 9, 2011.

Office Action from the State Intellectual Property Office of the P.R.C (SIPO) for application No. 200880013423, dated Jul. 29, 2011.

Ogawa et al., "Electrothrombosis as a Treatment of Cirsoid Angioma in the Face and Scalp and Varicosis of the Leg," Plastic and Reconstructive Surgery, vol. 70, No. 3, pp. 310-318, Sep. 1982.

O'Reilly, "A Technique of Diathermy Sclerosis of Varicose Veins," The Australian New Zealand Journal of Surgery, vol. 51, No. 4, pp. 379-382, Aug. 1982.

O'Reilly, "Endovenous Diathermy Sclerosis as a Unit of the Armamentarium for the Attack on Varicose Veins," The Medical Journal of Australia, p. 900, Jun. 1, 1974.

O'Reilly, "Endovenous Diathermy Sclerosis of Varicose Veins," The Australian New Zealand Journal of Surgery, vol. 47, No. 3, pp. 393-395, Jun. 1997.

Ricci et al., "Ambulatory Phlebectomy" $2^{nd}$ Edition, pp. 97-105, 187-211, 2005.

Sokolnicki et al., "Attempts to Coagulate Varices of the Lower Limbs with High-frequency Current," Polish Medical Weekly, Jul. 1966, No. 27, pp. 1024-1026.

Watts, Endovenous Diathermy Destruction of Internal Saphenous, British Medical Journal, Oct. 7, 1972.

U.S. Appl. No. 11/280,778, filed Nov. 16, 2005, Farley et al., 2006-0069417, Office Actions Feb. 6, 2009 Dec. 11, 2009 Oct. 21, 2010 Notice of Allowance Apr. 4, 2011.

U.S. Appl. No. 13/095,335, filed Apr. 27, 2011, Farley et al., 2011-0202047, Office Actions Aug. 5, 2011.

U.S. Appl. No. 12/110,169, filed Apr. 25, 2008, Stevens et al., 2008-0292255, Office Action Jul. 25, 2011 Oct. 18, 2011.

U.S. Appl. No. 12/110,169, filed Apr. 25, 2008, Stevens et al., 2008-0292255, Office Action Feb. 3, 2012.

U.S. Appl. No. 13/095,335, filed Apr. 27, 2011, Brian E. Farley, 2011/0202047, Office Action Mar. 2, 2012.

\* cited by examiner

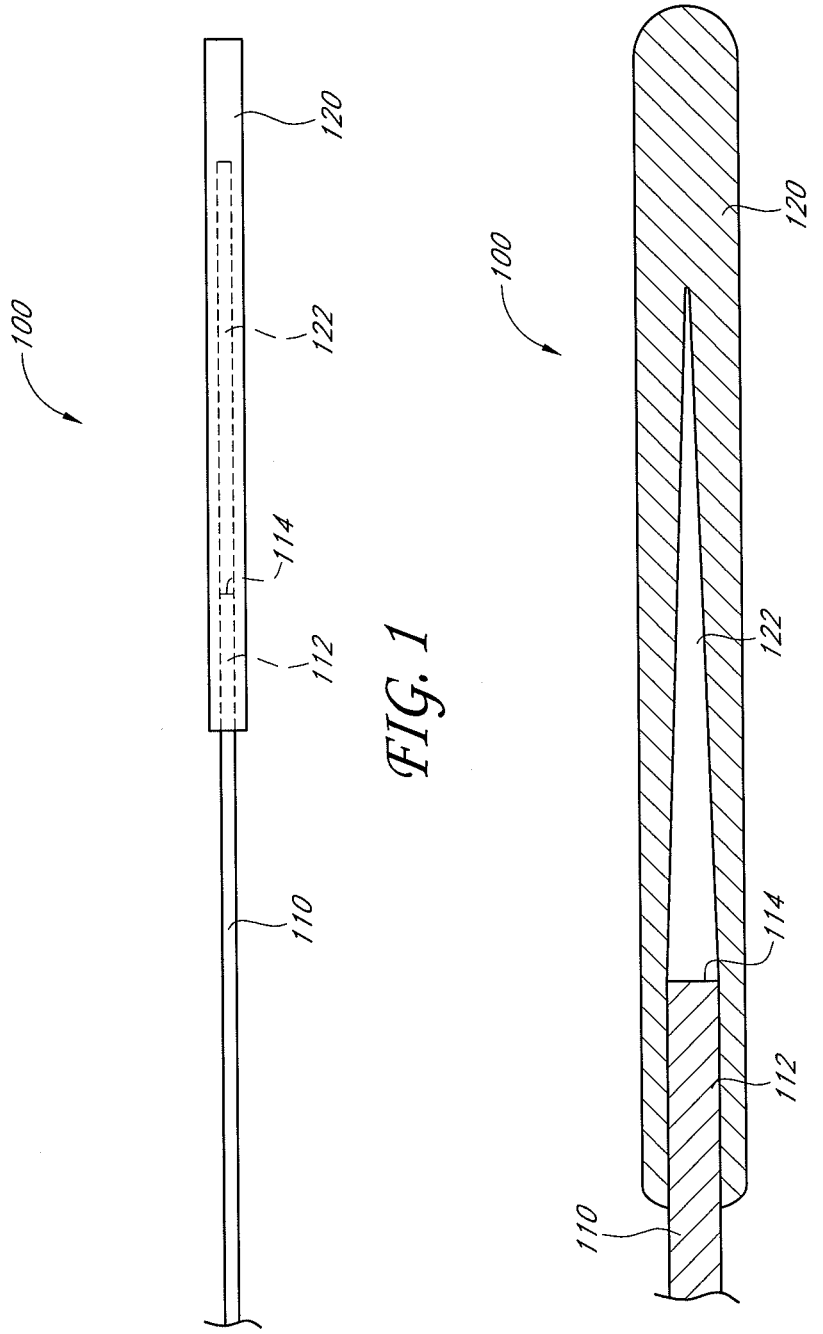

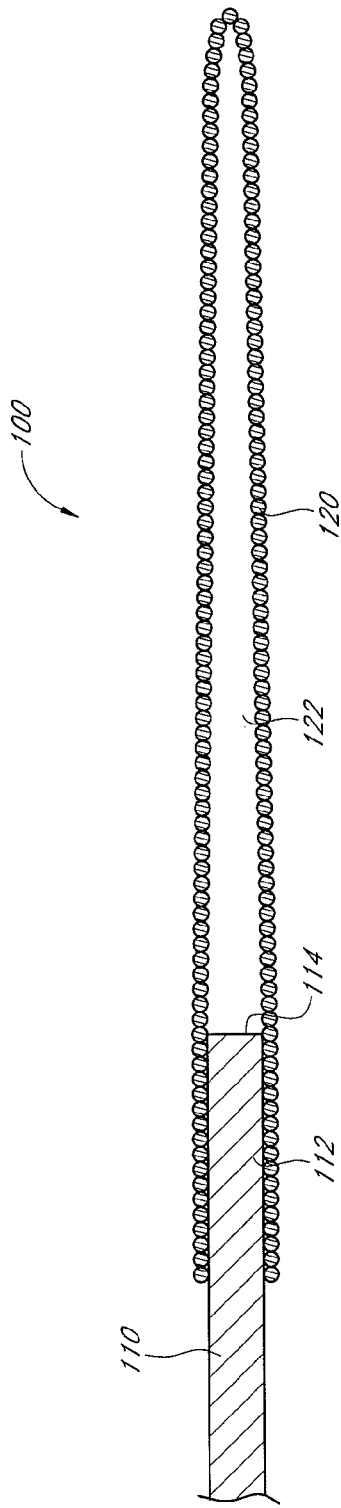
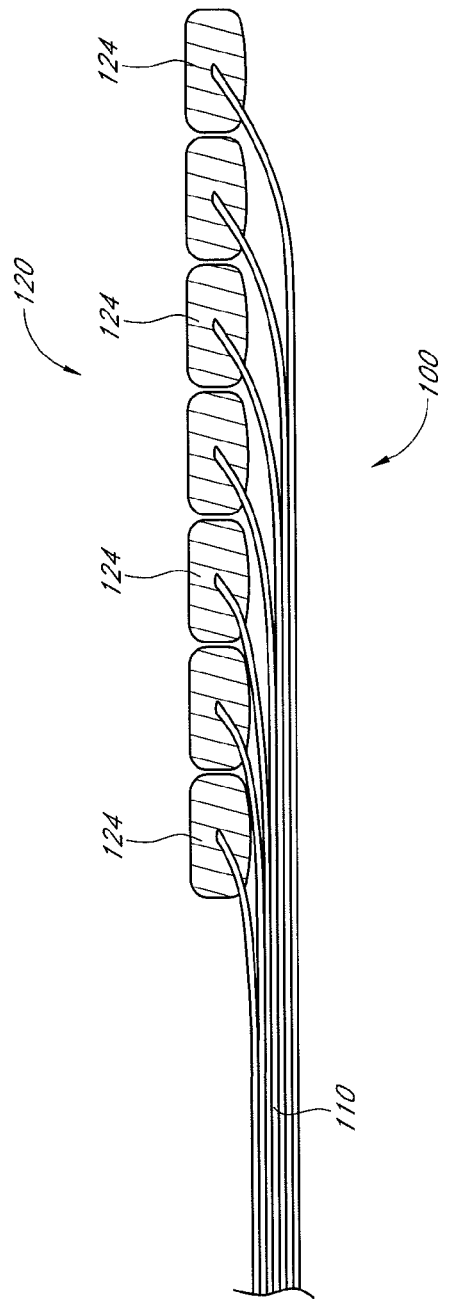

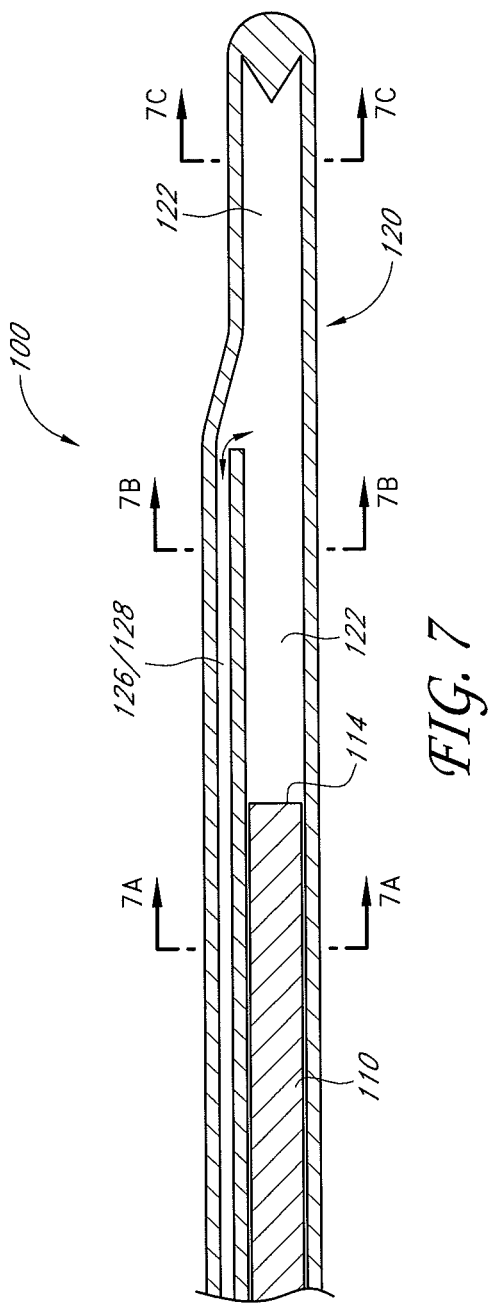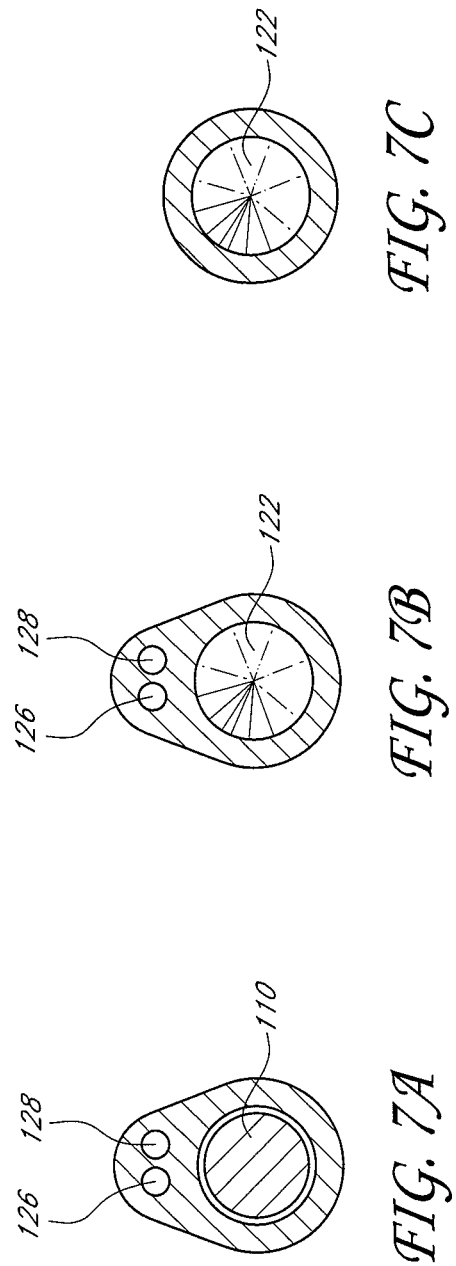

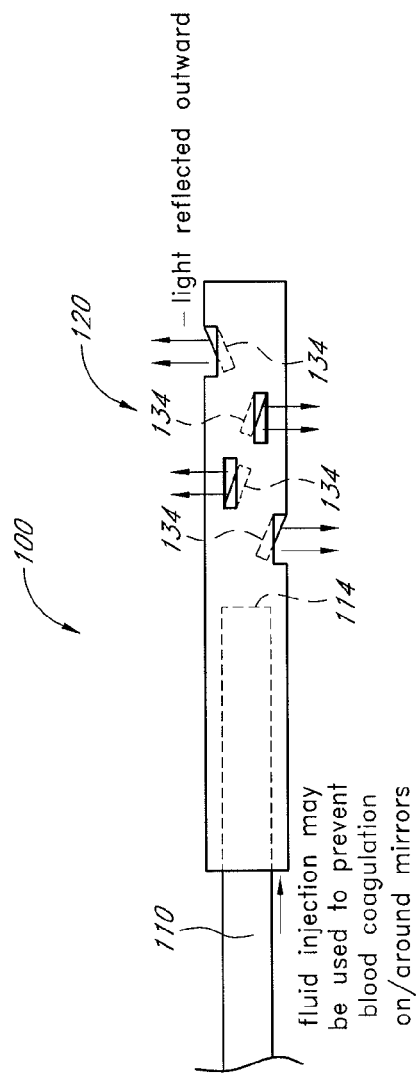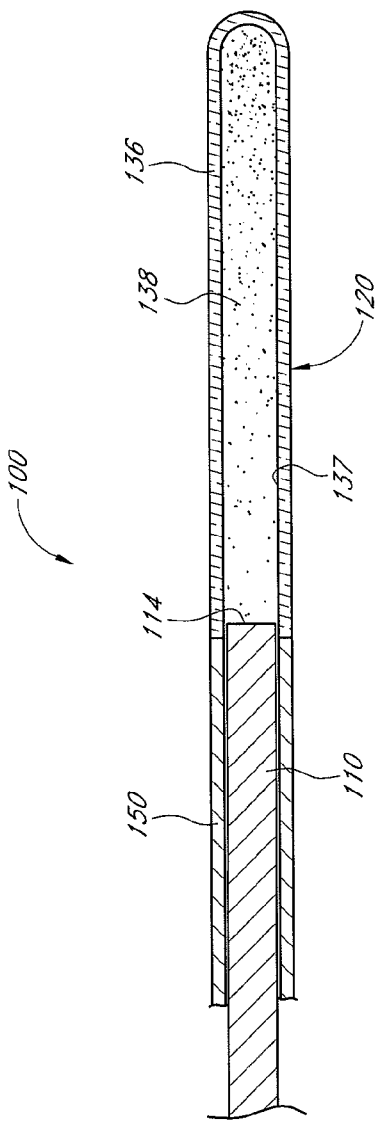
FIG. 12
FIG. 13

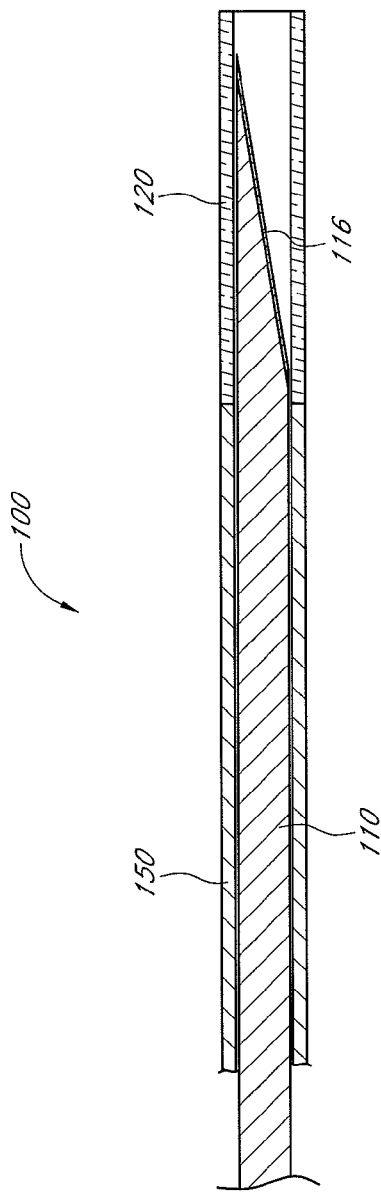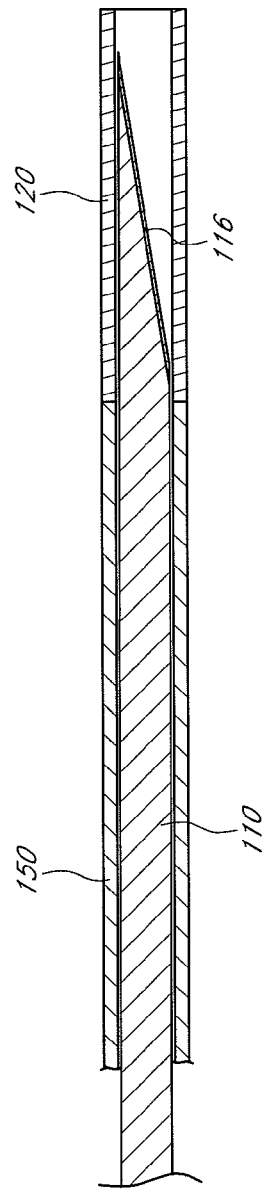

ENERGY DEVICES AND METHODS FOR TREATING HOLLOW ANATOMICAL STRUCTURES

CROSS-REFERENCE TO RELATED APPLICATIONS

This application claims the benefit under 35 U.S.C. §119 (e) of U.S. Provisional Application No. 61/058,874, filed Jun. 4, 2008; which is hereby incorporated by reference herein and made a part of this specification.

BACKGROUND

Field of the Invention

This application is related to the use of optical fibers for treating hollow anatomical structures within a body.

Description of the Related Art

Optical fibers have been used in conjunction with laser systems to treat venous reflux for several years. The procedure involves placing an optical fiber in the vein and transmitting laser light through the fiber to the vein walls, causing the vein to close. In current vein ablation systems, an optical fiber is inserted into the vein, either bare or through an introducer sheath. In the latter case, the fiber tip is positioned outside and distal of the distal end of the introducer sheath during the procedure. In either case, when laser light is transmitted to the fiber, the fiber tip may become very hot, potentially causing its cladding and/or buffer material to burn inside the patient's body. In addition, if a hot fiber tip contacts the vein wall, it may cause perforations which can result in bruising and patient discomfort.

SUMMARY OF THE INVENTION

An apparatus for treating a hollow anatomical structure can comprise an optical fiber having a treatment end configured to emit light energy and an elongate energy application device. The elongate energy application device can comprise a mass of heat-conducting material coupled to the treatment end of the optical fiber and forming a narrowing, elongate internal chamber.

The optical fiber of some embodiments of the apparatus can be configured to emit light energy from the treatment end that impinges on the sidewalls of the narrowing, elongate internal chamber. This can be done substantially without back-reflection of the light energy into the optical fiber. As light energy impinges, light energy can be converted to heat energy along the length of the elongate internal chamber, heating the heat conductive material so that the elongate energy application device can apply heat energy to surrounding anatomy, treating a corresponding length of a hollow anatomical structure.

In some embodiments, the narrowing, elongate internal chamber can generally narrow with distance, as measured from the treatment end of the fiber, wherein the sidewalls approach each other and eventually come together at the far end of the chamber from the treatment end of the optical fiber.

According to some embodiments of an apparatus having an internal chamber, the internal chamber is substantially conical, pyramidal or wedge shaped and/or a portion of the energy application device distal of treatment end of the optical fiber is between about 2 and 10 centimeters long. The apparatus can be configured for segmental ablation of the hollow anatomical structure.

A method of treating a hollow anatomical structure having an inner wall can comprise inserting, into the hollow anatomical structure, a catheter having an energy application device with a narrowing, elongate internal chamber coupled to a fiber optic tip of an optical fiber and passing light energy through the optical fiber and converting the light energy to heat energy via sidewalls of the chamber. The method may further comprise applying the heat energy to a one centimeter or greater length of the inner wall in a first treatment segment of the hollow anatomical structure with the energy application device, moving the energy application device to one or more additional treatment segments of the hollow anatomical structure and applying the heat energy to a one centimeter or greater length of the inner wall in the one or more additional treatment segments of the hollow anatomical structure with the energy application device.

In some embodiments of a method the elongate energy application device comprises a mass of heat-conducting material coupled to the treatment end of the optical fiber and forming the elongate internal chamber that generally narrows with distance, as measured from the treatment end of the fiber, wherein the sidewalls approach and eventually come together at the far end of the chamber from the treatment end of the optical fiber. Certain methods can further comprise a step of emitting light energy from the fiber optic tip that impinges on the sidewalls of the narrowing, elongate internal chamber—substantially without back-reflection of the energy into the optical fiber.

In certain of the disclosed methods converting light energy to heat energy can comprise doing so along the length of the elongate internal chamber thereby heating the heat-conductive material or doing so along a length of the energy application device. Also, in further embodiments the length of wall that is treated in each of the treatment segments can correspond to the length of the energy application device along which light energy is converted to heat energy.

Some embodiments of a method comprise applying the heat energy to a one centimeter or greater length of the inner wall in the first treatment segment of the hollow anatomical structure while the energy application device is stationary in the first treatment segment and may also include doing so while the energy application device is stationary in the one or more additional treatment segments.

A hollow anatomical structure treatment device according to certain embodiments can comprise an optical fiber having a fiber tip, and an end capsule having a chamber therein. The end capsule can enclose a fiber tip; and media distal of the fiber tip. According to some embodiments, the media establishes a gradient within the chamber such that at least one of absorption, scattering and reflectance of laser energy from the optical fiber increases as a function of the distance from the fiber tip.

An apparatus can be for treating a blood vessel having an inner wall. The apparatus can comprise an optical fiber having a treatment end configured to emit light energy and means, coupled to the treatment end of the optical fiber, for both (a) converting the light energy to heat energy and (b) applying the heat energy to a one centimeter or greater length of the inner wall of the blood vessel.

The means for converting and applying can comprise a mass of heat-conducting material that forms an elongate internal chamber that tapers inward as it extends away from the optical fiber along the longitudinal axis of the fiber. In some embodiments, the means for converting and applying comprises an elongate mass of conductive metal material and/or a metallic wire coil. In certain embodiments, the means for converting and applying distal of the treatment end of the optical fiber is between about 2 and 10 centimeters long.

An optical fiber in some embodiments can be configured to emit light energy from the treatment end that impinges on inward-tapering sidewalls of the chamber—substantially without back-reflection of the light energy into the optical fiber—such that as light energy impinges, light energy is converted to heat energy along the length of the chamber, thereby heating the heat-conductive material.

BRIEF DESCRIPTION OF THE DRAWINGS

FIG. 1 depicts one embodiment of an HAS treatment device.

FIG. 2 depicts the distal portion of another embodiment of an HAS treatment device.

FIG. 3 depicts the distal portion of another embodiment of an HAS treatment device.

FIG. 4 depicts the distal portion of another embodiment of an HAS treatment device.

FIGS. 7 and 7A-C depict the distal portion of another embodiment of an HAS treatment device, and several sectional views taken along the length of the device.

FIG. 12 depicts the distal portion of another embodiment of an HAS treatment device.

FIG. 13 depicts the distal portion of another embodiment of an HAS treatment device.

FIG. 15 depicts one embodiment of an HAS treatment device employing the fiber optic of FIG. 14.

FIG. 16 depicts another embodiment of an HAS treatment device employing the fiber optic of FIG. 14.

DETAILED DESCRIPTION OF THE PREFERRED EMBODIMENTS

Figure 5:
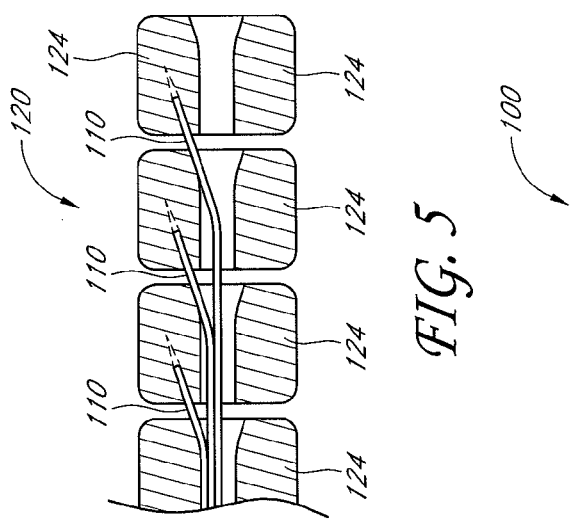
FIG. 5 depicts the distal portion of another embodiment of an energy application portion of an HAS treatment device.

The features of the systems and methods will now be described with reference to the drawings summarized above. The drawings, associated descriptions, and specific implementation are provided to illustrate preferred embodiments and not to limit the scope of the patent protection sought in connection with this specification.

In addition, methods and functions of treatment systems or devices described herein are not limited to any particular sequence, and the acts relating thereto can be performed in other sequences that are appropriate. For example, described acts may be performed in an order other than that specifically disclosed, or multiple acts may be combined in a single act.

Disclosed herein are embodiments of devices and methods for treating hollow anatomical structures, in particular blood vessels, veins, or varicose veins. The disclosed devices can be employed to heat the target hollow anatomical structure (or "HAS") to impart a therapeutic effect. In particular, with regard to blood vessels, veins, or varicose veins, the disclosed devices can be employed to heat the vessel/vein wall to cause the vessel/vein to shrink and thereby reduce or (when occlusion is achieved) eliminate or substantially eliminate the flow of blood through the treated vessel/vein.

The devices disclosed herein can be employed to practice any of the methods of HAS treatment disclosed in US Patent Application Publication No. 2007/0100405, published on May 3, 2007, the entirety of which is hereby incorporated by reference herein and made a part of this specification. In particular, the devices disclosed herein can be employed to perform, in whole or in part, any of the treatment methods depicted in FIGS. 16A-16D and described in paragraphs 0338-0352 of the above-referenced '405 publication. When employed in practicing such methods (or when practicing other methods described herein), the devices described herein can be similar to the HAS treatment system 200, HAS indexing treatment device 270 or catheter system 900/950 disclosed in the above-referenced '405 publication, except as described below.

The devices disclosed herein can be employed to practice endovascular methods of reducing the diameter of or occluding an HAS (such as a blood vessel or vein including a leg vein like the greater or lesser saphenous vein), which methods can involve inserting the device into the lumen of the HAS; positioning the energy application portion of the device at or near a first treatment site of the HAS; holding the device stationary in the HAS lumen while applying energy from the energy application portion to a length of greater than one centimeter (or of 2-10 centimeters) of the HAS wall at the first treatment site to heat the HAS wall and reduce its diameter; after applying energy to the first treatment site, moving the energy application portion to a second treatment site (which can be adjacent to or overlapping with the first treatment site) in the HAS lumen; and holding the device stationary in the HAS lumen while applying energy from the energy application portion to a length of greater than one centimeter (or of 2-10 centimeters) of the HAS wall at the second treatment site to heat the HAS wall and reduce its diameter. The foregoing can be repeated for a number of treatment sites until a desired contiguous length of the HAS has been treated. Optionally, the application of energy in any of these methods can comprise delivering laser or light energy to a heat-conducting energy application portion of the device. The energy application portion can be greater than 1 centimeter, or can be 2-10 centimeters, in length. In some embodiments there can be a small overlap between the different treatment sites.

In some embodiments indexing can be used to move the device according to indexed positions. The indexing can be for example, indexing marks on a catheter or introducer sheath.

A method of treating a hollow anatomical structure can comprise inserting, into a hollow anatomical structure, a catheter having an energy application device near a fiber optic tip of an optical fiber, applying energy such as heat to a length of wall of a first treatment segment of the hollow anatomical structure with or through the energy application device, moving the energy application device to one or more additional treatment segments of the hollow anatomical structure, there being at least a small overlap between each succeeding treatment segment and the prior treatment segment and applying energy to a length of wall of the one or more additional treatment segments of the hollow anatomical structure.

Another method of treating a hollow anatomical structure can comprise inserting, into a hollow anatomical structure, a catheter having an energy application device near a fiber optic tip of an optical fiber, applying energy to a length of wall of a first treatment location within the hollow anatomical structure with or through the energy application device, moving the energy application device an indexed amount to one or more additional treatment locations within the hollow anatomical structure and applying heat to a length of wall of the one or more additional treatment locations of the hollow anatomical structure.

A method of some embodiments of treating a hollow anatomical structure having an inner wall can comprise inserting, into the hollow anatomical structure, a catheter having an energy application device coupled to a fiber optic tip of an optical fiber, passing light energy through the optical fiber and converting the light energy to heat energy in the energy application device or passing light energy through the energy application device, applying the heat energy or light energy to a one centimeter or greater length of the inner wall in a first treatment segment of the hollow anatomical structure, moving the energy application device to one or more additional treatment segments of the hollow anatomical structure and applying the heat energy or light energy to a one centimeter or greater length of the inner wall in the one or more additional treatment segments of the hollow anatomical structure.

In some embodiments, a method of treating a hollow anatomical structure can comprise the steps of inserting, into a hollow anatomical structure, a catheter having an energy application device with a narrowing, elongate internal chamber that encloses a fiber optic tip of an optical fiber; applying heat to a length of wall of a first treatment segment of the hollow anatomical structure with the energy application device; moving the energy application device to one or more additional treatment segments of the hollow anatomical structure, there being at least a small overlap between each succeeding treatment segment and the prior treatment segment; and applying heat to a length of wall of the one or more additional treatment segments of the hollow anatomical structure.

In practicing any of the vein treatment methods disclosed or referenced herein, tumescent fluid or anesthesia can be applied to the perivenous tissue surrounding the desired treatment area to compress the vein wall nearer to or in apposition with the energy application portion of the device. Any of the methods disclosed in Goldman et al., U.S. Pat. No. 6,258,084, issued Jul. 10, 2001 (the entirety of which is hereby incorporated by reference herein) can be employed to deliver tumescent fluid or anesthesia when practicing any of the vein treatment methods disclosed or referenced herein.

FIG. 1 depicts one embodiment of an HAS treatment device 100. The device 100 includes an optical fiber 110 and an energy application portion or device 120 positioned at the distal end of the optical fiber 110. The energy application device 120 can take the form of a heat-conductive or heat-sink target which can comprise an elongate mass of heat-conductive material such as metal (aluminum, stainless steel, copper, titanium, etc.), ceramic, glass (e.g. borosilicate glass), or high temperature polymers. The optical fiber 110 can be any suitable endovascular optical fiber, for example a fiber having a size in the range of 200-1200 microns. Generally, the energy application portion 120 has a cross sectional size suitable for insertion into a vein, e.g. 2-12 French, and has a length greater than one centimeter (e.g. 2-10 centimeters). In use, laser or light energy is passed distally through the optical fiber 110 (and, in some embodiments, out the distal fiber tip 114) to or into the energy application device 120 to thereby heat the energy application device 120 to a desired treatment temperature (e.g., 70-120 degrees C.). When the device 100 is located in an HAS, the portions of the HAS adjacent the energy application device 120 are heated to the desired treatment temperature.

The energy application device 120 can be rigid, malleable or flexible. Materials and construction techniques can be selected to impart the desired properties to the device 120.

As depicted in FIG. 1, a distal section 112 of the optical fiber 110 can extend into and/or be embedded in a proximal region of the energy application device 120. The energy application device 120 can incorporate an elongate internal chamber 122 to receive incoming laser/light energy. As depicted, the chamber 122 can be coaxial with the optical fiber 110 and the energy application device 120. Where the chamber 122 is employed, a pressure vent (not shown) can be incorporated to avoid buildup of excess pressure in the chamber 122, or venting can be accomplished via articulation slots (see below) formed in the energy application device 120.

FIG. 2 depicts one variation of the chamber 122 in which the interior walls of the chamber 122 are formed in a conical, pyramidal or wedge shape (or otherwise angled or curved) to prevent back-reflection of laser/light into the fiber 110 and to promote distribution of the laser/light energy along the length of the target or energy application device 120.

FIG. 3 depicts an embodiment of the energy application device 120 comprising a metallic wire or ribbon wound into a tapered, enclosed coil.

In the embodiment of FIG. 4, the fiber optic 110 is multi-stranded, comprising a plurality or bundle of fibers, each of which is connected to an individual section 124 of the energy application device 120. The energy application device or target 120 therefore comprises a linear array of separate, discrete sections 124, each of which can be formed from any the materials disclosed herein as suitable for the energy application device 120. Each strand of the fiber optic 110 can be employed to direct laser/light energy into its corresponding section 124, which facilitates separate operation of the sections and fine control over the location where energy is applied to the HAS, and over the energy intensity and temperature profiles along the length of the energy application device 120.

FIG. 5 depicts a variation of the device 100 of FIG. 4, in which the sections 124 of the energy application device 120 are ring-shaped. This embodiment of the energy application device 120 therefore comprises a linear array of separate, discrete, coaxial ring-shaped targets.

Figure 6:
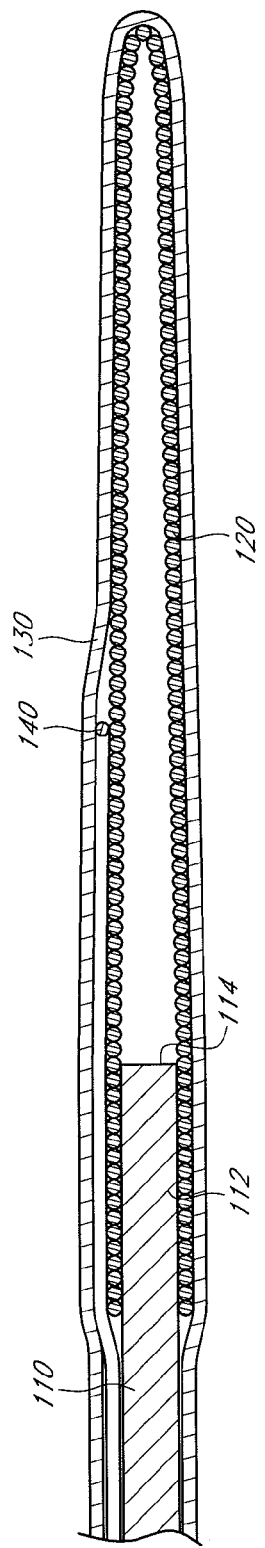
FIG. 6 depicts the distal portion of another embodiment of an HAS treatment device.

FIG. 6 depicts another embodiment of the HAS treatment device 100, incorporating an outer jacket 130 of non-stick material which substantially covers the energy application device 120 (and, if desired, portions of the fiber optic 100) to prevent coagulated material (e.g. blood, vein wall tissue) from sticking to the device 100. The jacket 130 can comprise Teflon, a hydrophobic surface material, nonreactive metal or the like. FIG. 6 depicts the jacket 130 over a coil type energy application device 120 (as in FIG. 3) but the jacket 130 can be employed with any of the energy application devices 120 disclosed herein.

Also shown in FIG. 6, one or more temperature sensors 140 can be incorporated near the outer surface of the energy application device 120, to provide temperature measurement and feedback to a control system (not shown) that regulates delivery of the laser/light to effect a desired device or operating temperature. The temperature sensor 140 can comprise anyone of or combination of a thermocouple, a thermistor, a fiber optic based sensor, or any other suitable temperature sensor. As with the jacket 130, the temperature sensor 140 can be employed with any of the energy application devices 120 disclosed herein.

FIGS. 7 and 7A-C depict the device 100 with an alternative type of energy application device 120 in the form of a fluid-based energy application device 120. A fluid, located in the chamber 122, may be chosen to have a boiling point matched to the desired treatment temperature (e.g. saline balanced to a boiling temperature of approximately 120 degrees C.). Such a device may have a vent lumen 126 configured to vent pressure from within the chamber 122 of the energy application device 120, and a supply lumen 128 to supply fluid to the energy application device as needed.

In one variation of the device 100 of FIG. 7, the energy application device 120 incorporates a plurality of steam vent ports (not shown) on its outer surface, which are in fluid communication with the chamber 122. Water delivered into the chamber 122 is heated via application of laser/light by the fiber optic 110 until it boils. The resulting steam is emitted through the vent ports and passes into thermal contact with the surrounding portion of the HAS, thereby heating the HAS to a desired treatment temperature. The vent ports can be configured to hold the steam in the chamber 122 until sufficient steam pressure develops, thereby opening the vent ports and permitting the steam to escape. In this device the vent lumen 126 may be omitted.

As a further variation of the devices of FIG. 7, the fluid employed may be a liquid which includes a suspension of fine particles therein, that reflect or absorb laser/light energy to enhance reflectance or heating effects.

The device 100 of FIG. 7, as well as the other devices 100 described herein, can optionally include an additional guidewire lumen or external structure configured to track over a suitable guidewire (e.g. a 0.035 inch, 0.025 inch, 0.018 inch or 0.014 inch guidewire).

Figure 8:
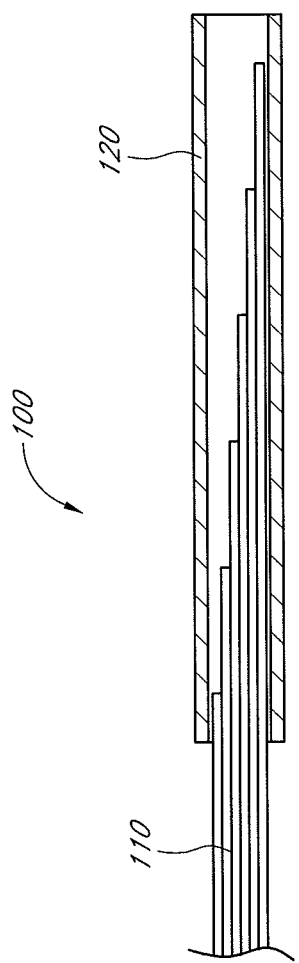
FIG. 8 depicts the distal portion of another embodiment of an HAS treatment device.

FIG. 8 depicts another embodiment of the HAS treatment device 100 employing a multi-strand fiber optic 110. In this embodiment, the terminations of the individual fiber strands are spaced longitudinally along the energy application device 120 to promote even heating of the energy application device 120 along its length. Each fiber strand is usable to deliver laser/light energy into the energy application device at the distal end or termination of each strand. Any of the energy application devices 120 disclosed herein can be used in this embodiment.

Figure 9:
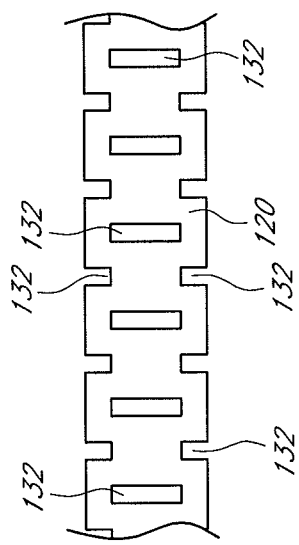
FIG. 9 depicts a configuration that may be employed in constructing the energy application portion of various depicted embodiments of the HAS treatment device.

FIG. 9 depicts a configuration that can be employed for forming the energy application device 120, such as that shown in FIGS. 1, 2 or 8. In this configuration, articulation slots 132 are cut into the sides of the energy application device 120 to make it more flexible. In the depicted embodiment the slots 132 are cut in a plane orthogonal to the longitudinal axis of the energy application device, with pairs of 180-degree opposed cuts whose position rotates by 90 degrees at each successive longitudinal position. Any other suitable configuration of the cuts may be used as well.

Figure 10:
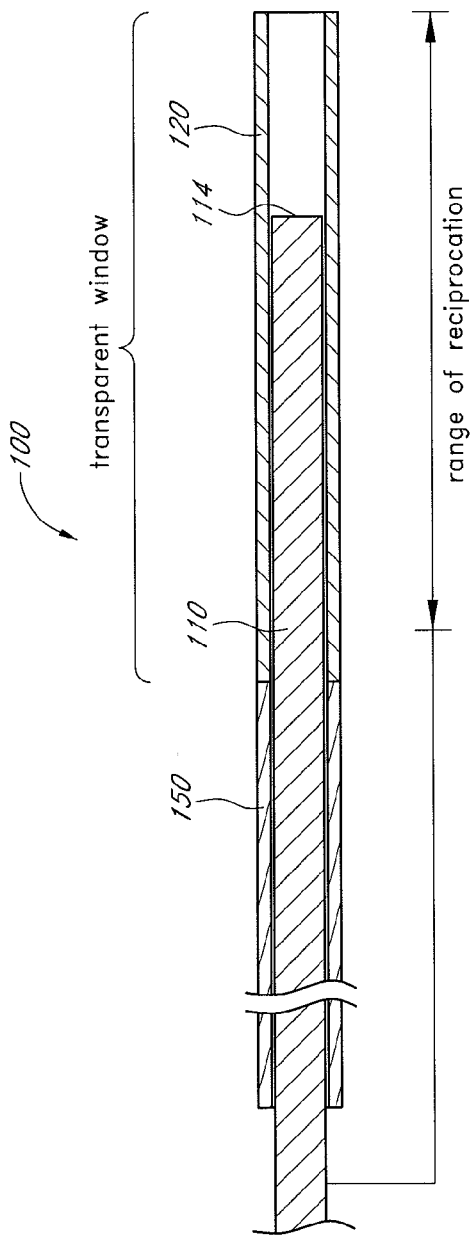
FIG. 10 depicts the distal portion of another embodiment of an HAS treatment device.

FIG. 10 depicts another embodiment of the HAS treatment device 100 wherein the energy application device 120 comprises a light-transmissive or transparent cylinder which is located at the distal end of a sheath 150. The cylinder 120 encloses the distal tip 114 of the fiber optic 110, which fiber and/or tip are configured to reciprocate longitudinally along the lumen of the cylinder 120 while emitting laser/light energy. The laser/light emitted from the fiber tip 114 passes through the cylinder walls to the HAS being treated. The reciprocation range of the fiber/tip can be the desired treatment length, e.g. greater than 1 centimeter, 2-10 centimeters, or 10 centimeters. During treatment of a given area of the HAS, multiple passes, or a single pass, of the fiber/tip through the reciprocation range can be made. After treating a first area of the HAS in this manner, the device 100 can be repositioned in the HAS to treat an adjacent area, with one end of the reciprocation range aligned with or overlapping the previously treated area. Before starting treatment of the new area, the fiber tip can be positioned at the aligned/overlapping edge of the reciprocation range, or it can be positioned in a random location within the reciprocation range. Optionally, a flow of saline, water or other liquid can be provided passing through the lumen of the sheath and cylinder and over the fiber tip 114 during treatment and/or emission of laser/light energy from the tip 114.

Figure 11:
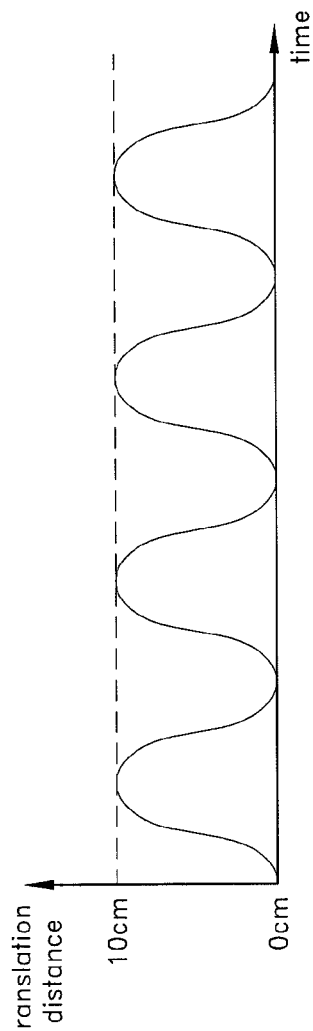
FIG. 11 depicts a reciprocation pattern for use with the fiber optic of the device of FIG. 10.

When using the device 100 of FIG. 10, the position change of the fiber tip 114 can be selected to achieve high uniformity of delivered energy along the treatment length or reciprocation range. One possible position change scheme is the sinusoidal pattern shown in FIG. 11.

FIG. 12 depicts another embodiment of the HAS treatment device 100 where the energy application device 120 comprises a tube (e.g. a sheath, slotted tube or the like) with reflectors 134 (e.g. mirror-polished portions) disposed in the light path extending longitudinally from the fiber tip 114. The reflectors 134 are configured to reflect the laser/light emitted from the fiber 110 radially outward through the sidewall of the energy application device, e.g. through holes cut in the side or an appropriately transmissive sidewall. In one embodiment, the reflectors 134 are mirror-polished tabs that are cut on three sides from the sidewall of the tube 120, and bent radially inwardly (about the fourth, uncut side) to form both an angled mirror that extends into the laser/light path, and an opening in the tube to permit reflected light to pass through the tube, radially outward to the HAS under treatment. The energy application device 120 can be coupled to or integrally formed with the distal end of a sheath 150 (see FIG. 10) through which the fiber 110 passes to the device 120. Optionally, a flow of saline, water or other liquid can be provided passing through the lumen of the sheath and device 120 and over the fiber tip 114 during treatment and/or emission of laser/light energy from the tip 114. As another option, the device 100 (or the sheath 150-device 120 assembly) can be rotated during application of energy to more evenly "scan" or distribute the laser/light over the HAS being treated.

FIG. 13 depicts another embodiment of the HAS treatment device 100 wherein the energy application device 120 comprises a transparent (or otherwise light-transmissive) capsule 136 (or a heat-sink target 136 such as a cylinder formed from metal or other suitable heat-conductive material disclosed above) having a chamber 137 filled with a variable-density fluid or gel 138 which is configured to heat uniformly along the length of the chamber 137 (or along the desired treatment length). The variable density can be achieved by altering the density of a chromophore that the emitted laser/light acts upon, with relatively little or minimal chromophore in the proximal region, near the fiber tip 114, and a relatively large or maximal amount of chromophore in the distal region, farthest from the fiber tip. As another option, the variable density can be achieved via light-scattering particles suspended in a transparent or highly transmissive gel, with particle density increasing as a function of distance away from the fiber tip 114. With either approach, an absorption gradient or a side-scattering or side-reflectance gradient is established in the material filling the chamber 137, with absorption/scattering/reflectance increasing as a function of distance from the fiber tip. Instead or in addition to such a gradient, the sidewalls of the capsule/heat-sink target 136 may vary in thickness as a function of distance from the fiber tip, with the thickest portion nearest the fiber tip and the thinnest portion farthest away. The capsule or heat-sink target 136 can be positioned at the distal end of a catheter or sheath 150. These approaches can be used alone or in combination to achieve uniform heating or light emission along the length of, and radially around, the capsule or heat-sink target 136.

In the device 100 of FIG. 13, an included temperature sensor (not shown) can be used to drive a desired treatment temperature, preferably sufficient to ablate the HAS being treated (e.g. 85-120 degrees C. or higher), yet not high enough to degrade the materials of the energy application device 120 (which can include an optional non-stick exterior coating).

Figure 14:
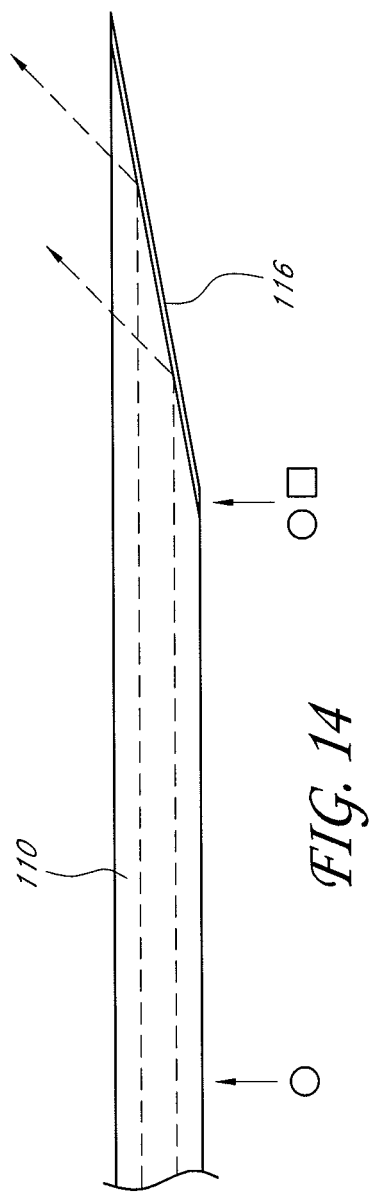
FIG. 14 depicts the distal portion of a fiber optic for use with the various depicted embodiments of the HAS treatment device.

FIG. 14 depicts one embodiment of an optical fiber 110 that can be employed with certain embodiments of the device 100 disclosed herein. The optical fiber 110 of FIG. 14 incorporates an angled, mirrored tip 116 which side-reflects the light/laser energy emitted from the fiber optic. This fiber can optionally be formed with a circular or non-circular (e.g. square or rounded-square) cross sectional shape. Preferably, the reflective tip 116 evenly distributes the laser/light energy along the length of the side-reflecting distal segment of the fiber.

FIG. 15 depicts one embodiment of an HAS treatment device comprising the fiber optic 110 of FIG. 14 and an energy application device 120 in the form of a transparent or highly transmissive cylinder connected to the distal end of a sheath 150. The cylinder 120 surrounds the side-reflecting distal portion of the fiber optic and permits laser/light energy emitted from the fiber 110 to pass radially through the cylinder and into the adjacent portion of the HAS being treated. Thus is provided a (preferably evenly) longitudinally distributed pattern of laser/light emitted from the energy application device 120. Optionally, a flow of saline, water or other liquid can be provided passing through the lumen of the sheath 150 and cylinder 120 and over the emitting portion of the fiber 110 during treatment and/or emission of laser/light energy from the fiber 110. As another option, the fiber 110 can be rotated during emission of laser/light, to further evenly distribute the energy being passed into the HAS tissue.

FIG. 16 depicts another embodiment of an HAS treatment device comprising the fiber optic 110 of FIG. 14 and an energy application device 120 in the form of a heat-conductive or heat-sink target 120 which can comprise cylinder of heat conductive material (e.g. any of the suitable materials disclosed above) connected to the distal end of a sheath 150. The cylinder 120 surrounds the side-reflecting distal portion of the fiber optic and heats up in response to laser/light energy emitted from the fiber 110. The heat in the cylinder 120 then passes radially from the cylinder and into the adjacent portion of the HAS being treated. Thus is provided a (preferably evenly) longitudinally distributed pattern of heat emitted from the energy application device 120. Optionally, a flow of saline, water or other liquid can be provided passing through the lumen of the sheath 150 and cylinder 120 and over the emitting portion of the fiber 110 during treatment and/or emission of laser/light energy from the fiber 110. As another option, the fiber 110 can be rotated during emission of laser/light, to further evenly distribute the energy being passed into the HAS tissue. As still another option, the fiber 110 of the devices 100 of FIGS. 15-16 can be axially reciprocated along the length of the cylinder 120 during laser/light emission.

In the device 100 of FIG. 16, one or more temperature sensors attached to or embedded in the heat-sink target 120 can be employed to provide temperature information to a controller that adjusts the power output of the laser energy source (not shown), the laser firing pulse duration, the fiber reciprocation and/or rotation speed, or any combination of the above to achieve uniform heating over the surface of the heat-sink target.

Any of the devices 100 disclosed herein can further include a laser energy source (not shown), which can comprise any suitable medical laser source, and which can be coupled to the fiber optic 110 to emit laser/light energy through the fiber 110 to the energy application device 120.

While certain embodiments have been described, these embodiments have been presented by way of example only, and are not intended to limit the scope of the disclosure or of the patent protection sought in connection with this specification. Indeed, the novel methods and systems described herein may be embodied in a variety of other forms; furthermore, various omissions, substitutions and changes in the form of the methods and systems described herein may be made without departing from the spirit of the disclosure.

What is claimed is:

1. An apparatus for treating a hollow anatomical structure, the apparatus comprising:
    an optical fiber having a treatment end configured to emit light energy; and
    an elongate energy application device comprising a mass of heat-conducting material coupled to the treatment end of the optical fiber and forming a narrowing, elongate internal chamber;
    wherein the optical fiber is configured to emit light energy from the treatment end that impinges on sidewalls of the narrowing, elongate internal chamber-substantially without back-reflection of the light energy into the optical fiber-such that as light energy impinges, light energy is converted to heat energy along the length of the elongate internal chamber, heating the heat-conductive material so that the elongate energy application device can apply heat energy to surrounding anatomy, treating a corresponding length of a hollow anatomical structure.

2. The apparatus of claim 1, wherein the narrowing, elongate internal chamber generally narrows with distance, as measured from the treatment end of the fiber, and wherein the sidewalls approach each other and eventually come together at the far end of the chamber from the treatment end of the optical fiber.

3. The apparatus of claim 1, wherein the internal chamber is substantially conical, pyramidal or wedge shaped.

4. The apparatus of claim 1, wherein the energy application device is an elongate mass of conductive metal material.

5. The apparatus of claim 1, wherein the energy application device is a metallic wire coil having an outer surface that is exposed for tissue contact.

6. The apparatus of claim 1, wherein a portion of the energy application device distal of the treatment end of the optical fiber is between about 2 and 10 centimeters long.

7. The apparatus of claim 1, further comprising a pressure vent to vent excess pressure from the elongate internal chamber.

8. The apparatus of claim 1, further comprising an outer jacket of non-stick material which substantially covers the energy application device.

9. The apparatus of claim 1, further comprising one or more temperature sensors.

10. The apparatus of claim 1, wherein the energy application device is configured for segmental ablation of a vein.

11. The apparatus of claim 10, wherein configured for segmental ablation of a vein comprises being configured for:
   insertion into the vein;
   application of heat to a length of wall of a first treatment segment of the vein with the energy application device;
   movement of the energy application device to one or more additional treatment segments of the vein; and
   application of heat to a length of wall of the one or more additional treatment segments of the vein.

12. An apparatus for treating a blood vessel having an inner wall, the apparatus comprising:
   an optical fiber having a treatment end configured to emit light energy; and
   means, coupled to the treatment end of the optical fiber, for both (a) converting the light energy to heat energy and (b) applying the heat energy to a one centimeter or greater length of the inner wall of the blood vessel.

13. The apparatus of claim 12, wherein the means for converting and applying comprises a mass of heat-conducting material that forms an elongate internal chamber that tapers inward as it extends away from the optical fiber along the longitudinal axis of the fiber.

14. The apparatus of claim 13, wherein the optical fiber is configured to emit light energy from the treatment end that impinges on inward-tapering sidewalls of the chamber-substantially without back-reflection of the light energy into the optical fiber-such that as light energy impinges, light energy is converted to heat energy along the length of the chamber, thereby heating the heat-conductive material.

15. The apparatus of claim 13, wherein the internal chamber is substantially conical, pyramidal or wedge shaped.

16. The apparatus of claim 13, wherein the means for converting and applying comprises an elongate mass of conductive metal material.

17. The apparatus of claim 13, wherein the means for converting and applying comprises a metallic wire coil having an outer surface that is exposed for tissue contact.

18. The apparatus of claim 13, wherein a portion of the means for converting and applying distal of the treatment end of the optical fiber is between about 2 and 10 centimeters long.

19. The apparatus of claim 13, further comprising a pressure vent to vent excess pressure from the elongate internal chamber.

20. The apparatus of claim 13, further comprising an outer jacket of non-stick material which substantially covers the means for converting and applying.

21. The apparatus of claim 13, further comprising one or more temperature sensors.

* * * * *